(12) United States Patent
Huang et al.

(10) Patent No.: US 12,678,070 B2
(45) Date of Patent: Jul. 14, 2026

(54) DEVICE AND METHOD FOR EVALUATING CERVICAL SPINE PROPRIOCEPTION

(71) Applicant: Taizhou People's Hospital, Taizhou (CN)

(72) Inventors: Aibing Huang, Beijing (CN); Meng Zhang, Fuyang (CN); Gaonian Zhao, Taizhou (CN); Lu Wang, Dingxi (CN)

(73) Assignee: Taizhou People's Hospital, Taizhou (CN)

( * ) Notice: Subject to any disclaimer, the term of this patent is extended or adjusted under 35 U.S.C. 154(b) by 395 days.

(21) Appl. No.: 18/515,281

(22) Filed: Nov. 21, 2023

(65) Prior Publication Data

US 2024/0188850 A1 Jun. 13, 2024

(30) Foreign Application Priority Data

Dec. 9, 2022 (CN) .......................... 202211584160.6

(51) Int. Cl.
A61B 5/11 (2006.01)
A61B 5/00 (2006.01)

(52) U.S. Cl.
CPC ........... A61B 5/1116 (2013.01); A61B 5/1114 (2013.01); A61B 5/1121 (2013.01);
(Continued)

(58) Field of Classification Search
CPC ... A61B 5/1116; A61B 5/1114; A61B 5/1121; A61B 5/4884; A61B 5/6803;
(Continued)

(56) References Cited

U.S. PATENT DOCUMENTS 6,969,360 B1 * 11/2005 Pai .......................... A61B 5/103
600/595
2014/0378808 A1 * 12/2014 Lee ...................... A61B 5/4812
600/300
(Continued)

FOREIGN PATENT DOCUMENTS

CN 109602424 A * 4/2019 ........... A61B 5/6802
CN 106805345 B * 5/2019 ............. A42B 3/048
(Continued)

*Primary Examiner* — Brian L Casler
(74) *Attorney, Agent, or Firm* — Hemisphere Law, PLLC

(57) ABSTRACT

A device and a method for evaluating cervical spine proprioception are provided. The method includes: taking a first head movement under a movement posture as a reference, calculating angle differences between multiple head movements under the same movement posture and the first head movement, and averaging the angle differences to obtain an average angle difference; then operating a data terminal to calculate average angle differences under multiple movement postures, and averaging the average angle differences to obtain a resultant average angle difference; comparing the resultant average angle difference with a standard value, thereby evaluating cervical spine proprioception of the subject based on a difference between the resultant average angle difference and the standard value. The disclosure can accurately evaluate position errors of a cervical spine under different postures, thereby avoiding errors caused by manual measurement.

8 Claims, 2 Drawing Sheets

(52) U.S. Cl.
CPC .......... *A61B 5/4884* (2013.01); *A61B 5/6803*
(2013.01); *A61B 5/7246* (2013.01)

(58) Field of Classification Search
CPC ..... A61B 5/7246; A61B 5/407; A61B 5/6814;
A61B 5/6801; A61B 5/6802; A61B
5/683; A61B 5/6831; A61B 5/70; A61B
5/702; Y02P 90/30
USPC ........................................................ 600/594
See application file for complete search history.

(56) References Cited

U.S. PATENT DOCUMENTS

2016/0374628 A1* 12/2016 Levine .................. A61B 5/1114
128/848
2017/0231490 A1* 8/2017 Toth ....................... A61B 3/113
600/558

FOREIGN PATENT DOCUMENTS

| CN | 210727748 U | * | 6/2020 | |
|----|-------------|---|--------|---|
| CN | 109938739 B | * | 7/2022 | |
| CN | 115919292 | * | 7/2023 | ........... A61B 5/1121 |

* cited by examiner

DEVICE AND METHOD FOR EVALUATING CERVICAL SPINE PROPRIOCEPTION

TECHNICAL FIELD

The disclosure relates to the field of medical equipment, and particularly to a device and a method for evaluating cervical spine proprioception.

BACKGROUND

Proprioception, also known as deep sensation, is a sensation produced by stimulating proprioceptors (muscle spindles, tendon spindles, etc.) in muscles, tendons, joints and periosteum using muscle contractions in the body. Proprioception plays an important role in the perception of limb position and movement, movement control and coordination. Cervical spine proprioception is one of the important references to evaluate the cervical spine function of a subject with cervical spondylosis. By performing accurate and targeted evaluations on cervical spine proprioception, an effective exercise rehabilitation plan can be determined.

At present, a method for evaluating the cervical spine proprioception is as follows: the subject wears a laser pen and an eye mask and sits up straight at a fixed distance of 90 centimeters (cm) from a target; and an evaluator records a starting position of a laser pen on a targeted white paper at the beginning, and records positions of the landing points of the subject's head turning back to the starting point after six directional movements of flexion and extension, left flexion and right flexion, and left and right rotation, then a distance between a starting point and a final landing point is measured, and a formula to convert the distance into an angle error. This evaluation method mainly has the following shortcomings: time-consuming, cumbersome process, and large error of manual measurement results. There is an urgent need for a more accurate and convenient device for evaluating cervical spine proprioception.

SUMMARY

In order to solve the above technical problems, the disclosure provides a device and a method for evaluating cervical spine proprioception to solve the problems in the related art. In order to achieve the above purpose of the disclosure, the technical solution adopted by the disclosure is as follows:

step 1, wearing a forehead band on a head of a subject, to locate a posture detection part at an inner side of the forehead band and on a forehead of the subject, and make an eye mask on the forehead band cover eyes of the subject;

step 2, starting, by an operator, a data terminal to connect the data terminal to the posture detection part;

step 3, performing, by the subject, one head movement under a target movement posture at prompt of the operator;

step 4, operating, by the operator, the data terminal to record an angle value of the head movement from the posture detection part; performing, by the subject, at least one head movement under the target movement posture under prompt of the operator, to thereby complete multiple head movements under the target movement posture, wherein the number of the multiple head movements is at least two; and operating, by the operator, the data terminal to record an angle value of each of the at least one head movement from the posture detection part;

step 5, changing, by the subject, the target movement posture, and repeating the step 3 and the step 4 to complete multiple target movement postures, wherein the multiple target movement postures include at least two of a forward flexion posture, a backward extension posture, a left rotation posture, a right rotation posture, a left flexion posture, or a right flexion posture;

step 6, operating, by the operator, the data terminal, thereby, taking, by the data terminal, the one head movement under each target movement posture of the multiple target movement postures as a reference, calculate an angle difference between each of the multiple the head movements under each target movement posture of the multiple target movement postures and the one head movement under each target movement posture of the multiple target movement postures to thereby obtain angle differences under each target movement posture of the multiple target movement postures, and averaging, by the data terminal, the angle differences to obtain an average angle difference under each target movement posture of the multiple target movement postures; wherein a formula for averaging the angle differences is as follows:

$$a = \frac{|\theta_n - \theta_1| + |\theta_{n-1} - \theta_1| + \cdots + |\theta_{n-(n-1)} - \theta_1|}{n-1}$$

where a represents the average angle difference under each target movement posture of the multiple target movement postures, n represents the number of the multiple head movements under the target movement posture, and $\theta$ represents an angle value measured by the posture detection part;

step 7, operating, by the operator, the data terminal to calculate a resultant average angle difference under the multiple movement postures; wherein a formula for calculating the resultant average angle difference is as follows:

$$y = \frac{a_1 + a_2 + \cdots + a_p}{p}$$

where y represents the resultant average angle difference, p represents the number of the multiple movement postures, and a represents the average angle difference under each target movement posture of the multiple target movement postures; and step 8, operating, by the operator, the data terminal, thereby, comparing, by the data terminal, the resultant average angle difference with a standard value, and evaluating, by the data terminal, cervical spine proprioception of the subject based on a difference between the resultant average angle difference and the standard value.

In an embodiment, the data terminal is a computer or a mobile phone, and a calculation program is installed on the data terminal and is configured for processing calculation of the formulas in the step 6 and the step 7.

A device for evaluating cervical spine proprioception, wherein the device is configured to implement the method for evaluating cervical spine proprioception as claimed in claim 1, the device includes the forehead band, and the inner side of the forehead band is provided with the posture detection part and the eye mask.

In an embodiment, a cloth bag is fixedly disposed on the inner side of the forehead band, an elastic block is disposed in the cloth bag, a mounting groove is defined on the elastic block, the posture detection part is inserted in the mounting groove, an outer surface of the cloth bag is fixedly connected to the eye mask, and the eye mask is disposed on the outer surface of the cloth bag.

In an embodiment, the elastic block is curved in shape.

In an embodiment, a covering part of the eye mask is disposed below the forehead band.

In an embodiment, two sides of the covering part of the eye mask are connected to two ends of an elastic band, and the elastic band is configured for being sleeved on a neck of the subject.

In an embodiment, the elastic band is provided with a first buckle.

In an embodiment, the forehead band is provided with a second buckle.

In an embodiment, the posture detection part includes a posture sensor, and the posture sensor is connected to the data terminal in a wired or wireless manner.

Compared with the prior art, the disclosure has the following beneficial effects: the disclosure can accurately evaluate position errors of the cervical spine under the forward flexion posture, the backward extension posture, the left rotation posture, the right rotation posture, the left flexion posture, and the right flexion posture, thereby avoiding errors caused by manual measurement. The disclosure can improve the evaluation accuracy of cervical spine proprioception by comparing the differences obtained through multiple detections with the standard value.

DETAILED DESCRIPTION OF EMBODIMENTS

Figure 1:
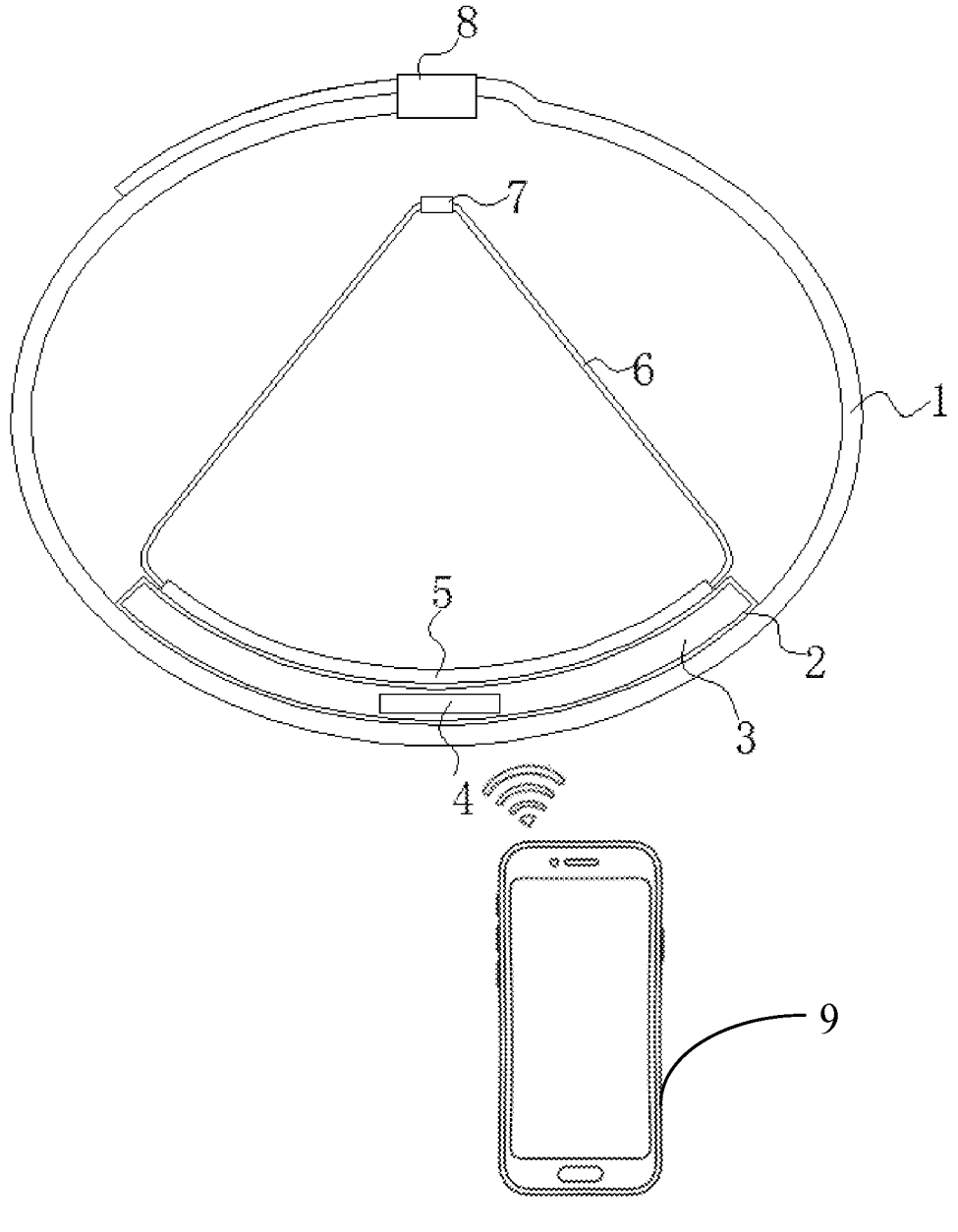
FIG. 1 illustrates a schematic top view of a device for evaluating cervical spine proprioception of the disclosure, in which a data terminal (for example, a mobile phone) is connected to a posture detection part of the device in a wireless manner.
Figure 2:
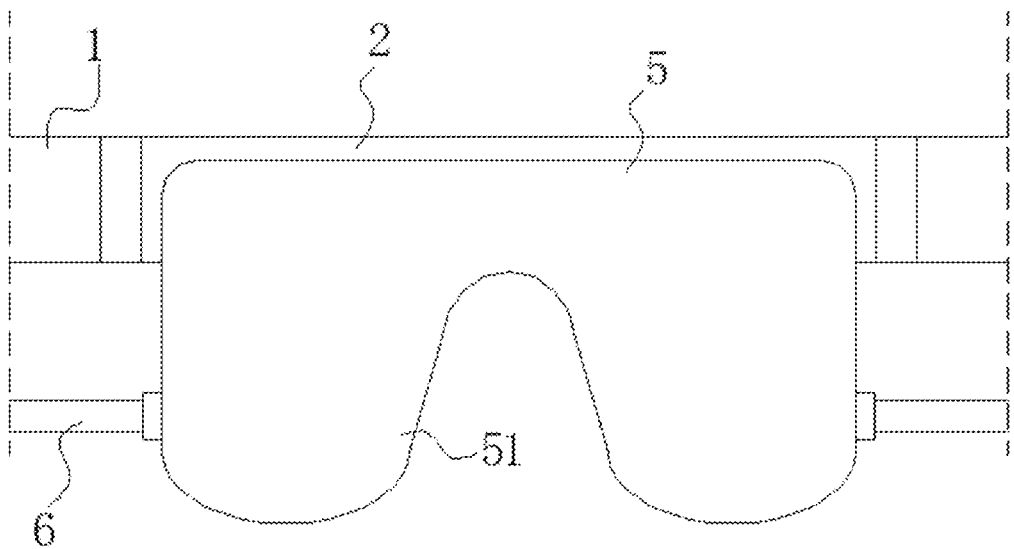
FIG. 2 illustrates a schematic diagram of a connection relationship between an eye mask and other components of the device for evaluating cervical spine proprioception of the disclosure.
Figure 3:
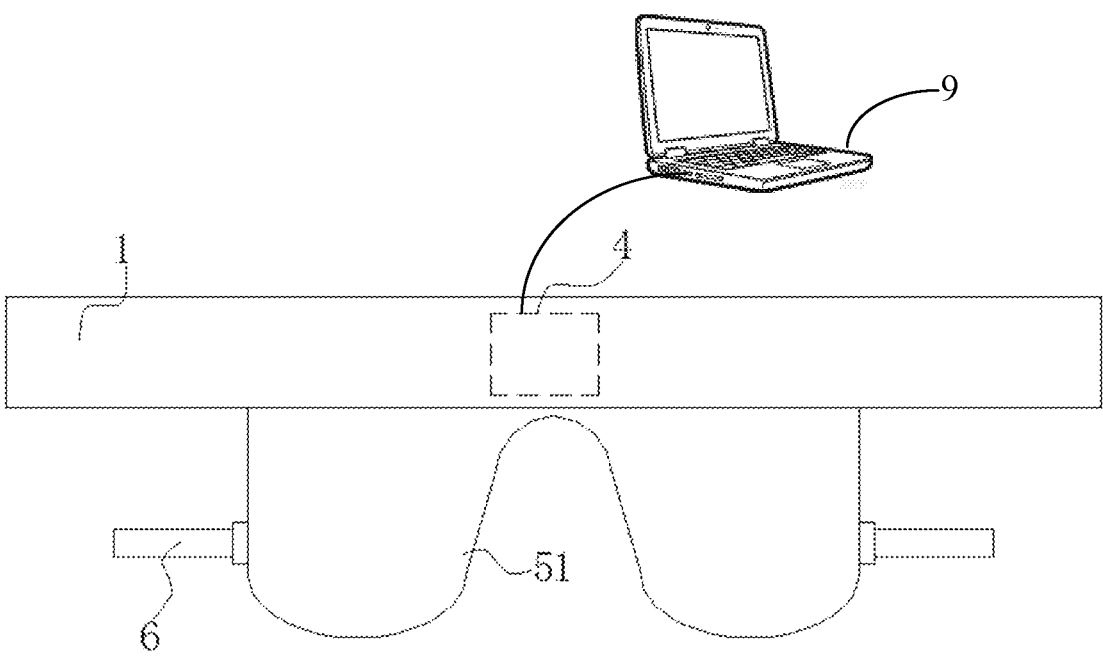
FIG. 3 illustrates a schematic diagram of a front view of the device for evaluating cervical spine proprioception of the disclosure, in which a data terminal (for example, a computer) is connected to a posture detection part of the device in a wired manner.

The technical solutions in the embodiments of the disclosure will be clearly and completely described below with reference to FIGS. 1 to 3 of the embodiments of the disclosure. Apparently, the described embodiments are only a part of the embodiments, but not all of them. Unless otherwise specified, the technical means used in the embodiments are conventional means well known to those skilled in the art.

A method for evaluating cervical spine proprioception provided by the disclosure includes:

step 1, wearing a forehead band 1 on a head of a subject; wherein a posture detection part 4 is located on an inner side of the forehead band 1 and on a forehead of the subject, and an eye mask 5 on the forehead band 1 covers eyes of the subject;

step 2, starting a data terminal 9 to connect the posture detection part 4;

step 3, performing a head movement of the subject at prompt of an operator;

step 4, using the data terminal 9 to record posture angle data of the head movement under operations of the operator, performing a next head movement under the prompt of the operator, completing at least two head movements under one movement posture;

step 5, changing movement postures of the subject and repeating the steps 3 and the step 4, wherein the movement postures include a forward flexion posture, a backward extension posture, a left rotation posture, a right rotation posture, a left flexion posture, and a right flexion posture;

step 6, operating the data terminal 9, taking a first head movement under one movement posture as a reference, calculating angle differences between the at least two head movements under one movement posture and the first head movement, and averaging the angle differences to obtain an average angle difference; wherein a formula for averaging the angle differences is as follows:

$$a = \frac{|\theta_n - \theta_1| + |\theta_{n-1} - \theta_1| + \cdots + |\theta_{n-(n-1)} - \theta_1|}{n-1}$$

where a represents the average angle difference under one movement posture, n represents the number of the at least two head movements under one movement posture, and θ represents an angle value measured by the posture detection part;

step 7, operating the data terminal 9 to calculate a resultant average angle difference under the movement postures; wherein a formula for calculating the resultant average angle difference is as follows:

$$y = \frac{a_1 + a_2 + \cdots + a_p}{p}$$

where y represents the resultant average angle difference, p represents the number of the movement postures, and a represents the average angle difference under one movement posture; and step 8, operating the data terminal 9 to compare the resultant average angle difference with a standard value, and evaluating cervical spine proprioception based on a difference between the resultant average angle difference and the standard value.

Specifically, when the subject performs five head movements, the formula for averaging the angle differences is as follows:

$$a = \frac{|\theta_n - \theta_1| + |\theta_{n-1} - \theta_1| + \cdots + |\theta_{n-(n-1)} - \theta_1|}{n-1}.$$

When the subject performs four movement postures which are the forward flexion posture, the backward extension posture, the left rotation posture, and the right rotation posture, a formula for calculating the resultant average angle difference is as follows:

$$y = \frac{a_1 + a_2 + \cdots + a_p}{p}.$$

Furthermore, in the step 3, the operator prompts the subject to perform multiple head movements, and each head movement is in the same posture. For example, the operator prompts "Please perform five forward flexion movements, and try to keep the same angle of movement". For the subject, what the subject needs to do is to perform the first head movement firstly, and then subsequent head movements should be performed based on the angle of the first head movement as far as possible. Since the eyes of the subject are covered by the eye mask 5, the subject can only move the head by proprioception.

The head movements performed by the subject in the same movement posture should be the same. For example, when the subject performs multiple head movements under the forward flexion posture, in step 4, only when the subject performs at least two head movements in the same movement posture, an angle difference between the first head movement and another head movement can be obtained, that is to say, n is more than or equal to two in the step 6. In the step 4, it is preferable to carry out five head movements. According to the health status of the subject, the number of head movements under the same movement posture can be set correspondingly, and the specific number of head movements is prompted by the operator.

The standard value is a resultant average angle difference obtained by evaluating a healthy subject, and the standard value is usually in a range of 5-10. The standard value can also be adjusted comprehensively according to the health status, age and other information of the subject. If the resultant average angle difference of the subject is greater than the standard value, it means that the subject cannot feel the cervical spine effectively and accurately in the process of multiple head movements, it also indicates that the cervical spine of the subject is in a poor condition, and the larger the difference between the resultant average angle difference and the standard value, the more it indicates that the subject is unable to effectively and accurately sense proprioception.

An evaluation process is specifically illustrated by one embodiment below.

In the embodiment, the subject performs five head movements under the same movement posture. When the subject performs five head movements under a forward flexion posture, angle values detected by the detection module 4 are 10, 9, 6, 12, and 15. When the subject performs five head movements under a backward extension posture, angle values detected by the detection module 4 are 14, 8, 19, 12, and 15. For the convenience of description, only the forward flexion posture and the backward extension posture are set in the embodiment, and more movement postures can be detected as required in specific implementation.

In a specific embodiment, a subject is sitting on a chair, wearing a forehead belt 1, and covering eyes with an eye mask 5. Then an operator starts a data terminal 9 connected to a posture detection part 4 to prompt the subject "please perform a first head movement under a forward flexion posture". The operator operates the data terminal 9 to record posture angle data, and then prompts the subject "please perform a second head movement under the forward flexion posture and keep the same angle as the first time, and the operator operates the data terminal 9 to record posture angle data. Five head movements under the forward flexion posture are performed in the same manner. Then the operator prompts the subject to change the movement posture for performing five head movements under a backward extension posture.

After the subject performs five head movements under the forward flexion posture, the operator inputs angle values including 10, 9, 6, 12, and 15 into a calculation program of the data terminal 9. The calculation program executes calculation of the formula in the step 6 to calculate an average angle difference under the forward flexion posture, thereby obtaining the average angle difference under the forward flexion posture is 3. After the subject performs five head movements under the backward extension posture, the operator inputs angle values including 14, 8, 19, 12, and 15 into the calculation program of the data terminal 9. The calculation program executes calculation of the formula in the step 6 to calculate an average angle difference under the backward extension posture, thereby obtaining the average angle difference under the backward extension posture is 3.5. Then the two average angle differences are inputted into the calculation program, the calculation program executes calculation of the formula in the step 7 to obtain a resultant average angle difference being 3.75. Compared with the standard value in a range of 5-10, the resultant average angle difference is less than the standard value, and it can be evaluated that the subject has good cervical proprioception.

Compared with the prior art, the disclosure can accurately evaluate position errors of the cervical spine under the forward flexion posture, the backward extension posture, the left rotation posture, the right rotation posture, the left flexion posture, and the right flexion posture, thereby avoiding errors caused by manual measurement. The disclosure can improve the evaluation accuracy of cervical spine proprioception by comparing the differences obtained through multiple detections with the standard value. The disclosure has a broad market application prospect in evaluating cervical spine proprioception.

In an embodiment, the data terminal 9 is a computer or a mobile phone, and a calculation program is installed on the data terminal 9 and is used for processing calculation of the formulas in the step 6 and the step 7.

Specifically, the computer and the mobile phones are devices that contain the calculation program integrated in a corresponding client program or an application.

A device for evaluating cervical spine proprioception provided by the disclosure adopts the method for evaluating cervical spine proprioception, and the device includes a forehead band 1. The inner side of the forehead band 1 is provided with the posture detection part 4 and the eye mask 5.

In an embodiment, a cloth bag 2 is fixedly disposed on the inner side of the forehead band 1. An elastic block 3 is disposed in the cloth bag 2. A mounting groove is defined on the elastic block 3. The posture detection part 4 is inserted in the mounting groove. An outer surface of the cloth bag 2 is fixedly connected to the eye mask 5. The eye mask 5 is disposed on the outer surface of the cloth bag 2.

Specifically, the forehead band 1 is a nylon band configured to be sleeved on the head of the subject. The forehead band 1 is located at a height of the forehead. In a locking process of the forehead band 1, the forehead band 1 is relatively fixed with the head of the subject, so as to prevent the posture detection part 4 from loosening. The elastic block 3 is configured to provide a pre-tightening force to tighten the forehead band 1 and facilitate the installation and fixation of the posture detection part 4. The elastic block 3 may be a rubber block.

In an embodiment, the elastic block 3 is curved in shape.

A covering part 51 of the eye mask 5 is disposed below the forehead band 1.

Specifically, the covering part 51 is configured to cover eyes of the subject. The covering part 51 is disposed below the forehead band 1, which can fully cover the eyes.

The eye mask 5 can be connected to the cloth bag 2 by sewing. The cloth bag 2 can be connected to the forehead band 1 by sewing. The forehead band 1 forms an annular structure. The cloth bag 2 is disposed on the inner side of the forehead band 1 and is located at the forehead of the subject. The eye mask 5 is located at the inner side of the annular structure of the forehead band 1.

In an embodiment, two sides of the covering part 51 of the eye mask 5 are connected to two ends of an elastic band 6, and the elastic band 6 is configured for being sleeved on a neck of the subject.

In an embodiment, the elastic band 6 is located below the eye mask 5. The forehead band 1 is located above the elastic band 6 and is located at a height of the forehead of the subject, the elastic band 6 is sleeved on the neck of the subject, and the elastic band 6 can tighten the covering part 51 of the eye mask 5 to fit the eyes of the subject, thereby improving the covering effect.

In an embodiment, the elastic band 6 is provided with a first buckle 7.

In an embodiment, the forehead band 1 is provided with a second buckle 8.

The first buckle 7 is configured to the tightness of the elastic band 6. The second buckle 8 is configured to the tightness of the forehead band 1.

In an embodiment, the posture detection part 4 includes a posture sensor, and the posture sensor is connected to the data terminal 9 in a wired or wireless manner.

Specifically, the posture detection part is an integrated module which is integrated with a posture sensor, a memory, a wireless module, etc. The posture sensor may be a three-axis sensor, and the posture sensor is configured to calculate three-axis angle data through a Kalman filtering fusion algorithm based on three-axis acceleration acquired by a chip, a gyroscope, and magnetic field data.

The above embodiments are only a part of embodiments of the disclosure, and the above embodiments are not intended to limit the scope of the disclosure. On a premise of not deviating from the design spirit of the disclosure, all kinds of changes, modifications, and replacements made by those skilled in the art based on the technical solutions of the disclosure should fall within the scope of protection defined in the claims.

What is claimed is:

1. A method for evaluating cervical spine proprioception, comprising:

step 1, wearing a forehead band (1) on a head of a subject, to locate a posture detection part (4) at an inner side of the forehead band (1) and on a forehead of the subject, and make an eye mask (5) on the forehead band (1) cover eyes of the subject, wherein the posture detection part (4) comprises a posture sensor, and the posture sensor is configured for connecting to a data terminal (9) in a wired or wireless manner;

step 2, starting, by an operator, the data terminal (9) to connect the data terminal (9) to the posture detection part (4), wherein the data terminal (9) is a computer or a mobile phone;

step 3, performing, by the subject, one head movement under a target movement posture at prompt of the detector operator;

step 4, operating, by the operator, the data terminal (9) to record an angle value of the one head movement under the target movement posture from the posture detection part (4); performing, by the subject, at least one head movement under the target movement posture under prompt of the operator, to thereby complete a plurality of head movements under the target movement posture, wherein the plurality of head movements under the target movement posture includes the one head movement under the target movement posture and the at least one head movement under the target movement posture, a total number of the plurality of head movements under the target movement posture is at least two; and operating, by the operator, the data terminal (9) to record an angle value of each of the at least one head movements under the target movement posture from the posture detection part (4);

step 5, changing, by the subject, the target movement posture, and repeating the step 3 and the step 4 to complete a plurality of target movement postures, wherein the plurality of target movement postures comprise at least two of a forward flexion posture, a backward extension posture, a left rotation posture, a right rotation posture, a left flexion posture, or a right flexion posture;

step 6, operating, by the operator, the data terminal (9), thereby, taking, by the data terminal (9), the one head movement performed in the step 3 under each target movement posture of the plurality of target movement postures as a reference, calculate an angle difference between each of the plurality of head movements under each target movement posture of the plurality of target movement postures and the one head movement performed in the step 3 under each target movement posture of the plurality of target movement postures to thereby obtain angle differences under each target movement posture of the plurality of target movement postures, and averaging, by the data terminal (9), the angle differences to obtain an average angle difference under each target movement posture of the plurality of target movement postures; wherein a formula for averaging the angle differences is as follows:

$$a = \frac{|\theta_n - \theta_1| + |\theta_{n-1} - \theta_1| + \cdots + |\theta_{n-(n-1)} - \theta_1|}{n - 1}$$

where a represents the average angle difference under each target movement posture of the plurality of target movement postures, n represents the total number of the plurality of head movements under the target movement posture, and θ represents an angle value measured by the posture detection part (4);

step 7, operating, by the operator, the data terminal (9) to calculate a resultant average angle difference under the plurality of movement postures; wherein a formula for calculating the resultant average angle difference is as follows:

$$y = \frac{a_1 + a_2 + \cdots + a_p}{p}$$

where y represents the resultant average angle difference, p represents a total number of the plurality of movement postures, $a_1$ represents an average angle difference under a first target movement posture of the plurality of target movement postures, $a_2$ represents an average angle difference under a second target movement posture of the plurality of target movement postures, and $a_p$ represents an average angle difference under a p-th target movement posture of the plurality of target movement postures; and step 8, operating, by the operator, the data terminal (9), thereby, comparing, by the data terminal (9), the resultant average angle difference with a standard value, and evaluating, by the data terminal (9), cervical spine proprioception of the subject based on a difference between the resultant average angle difference and the standard value.

2. The method for evaluating cervical spine proprioception as claimed in claim 1, wherein a calculation program is installed on the data terminal (9) and is configured for processing calculation of the formulas in the step 6 and the step 7.

3. A device for evaluating cervical spine proprioception, comprising:

a forehead band (1) configured to be sleeved on a head of a subject, an eye mask (5) configured to cover eyes of the subject, a cloth bag (2), a posture detection part (4) configured to measure angle values of head movements of the subject, and an elastic block (3) configured to provide a pre-tightening force to tighten the forehead band (1), wherein the posture detection part (4) comprises a three-axis sensor;

wherein the cloth bag (2) is fixedly disposed on an inner side of the forehead band (1), the eye mask (5) is disposed on an outer surface of the cloth bag (2), the cloth bag (2) is located between the eye mask (5) and the forehead band (1), the elastic block (3) is disposed in the cloth bag (2), and the posture detection part (4) is disposed in the elastic block (3).

4. The device for evaluating cervical spine proprioception as claimed in claim 3, wherein the elastic block (3) is curved in shape.

5. The device for evaluating cervical spine proprioception as claimed in claim 3, wherein a covering part (51) of the eye mask (5) is disposed below the forehead band (1).

6. The device for evaluating cervical spine proprioception as claimed in claim 5, wherein two sides of the covering part (51) of the eye mask (5) are connected to two ends of an elastic band (6).

7. The device for evaluating cervical spine proprioception as claimed in claim 6, wherein the elastic band (6) is provided with a first buckle (7).

8. The device for evaluating cervical spine proprioception as claimed in claim 3, wherein the forehead band (1) is provided with a second buckle (8).

* * * * *